United States Patent [19]
Farzin-Nia et al.

[11] Patent Number: 5,816,801
[45] Date of Patent: Oct. 6, 1998

[54] INSERT FOR REINFORCING AN ORTHODONTIC APPLIANCE AND METHOD OF MAKING SAME

[75] Inventors: Farrokh Farzin-Nia, Inglewood, Calif.; Rohit Chaman Lal Sachdeva, Plano, Tex.; Yoshiki Oshida, Dewitt, N.Y.

[73] Assignee: Ormco Corporation, Glendora, Calif.

[21] Appl. No.: 720,712

[22] Filed: Oct. 2, 1996

[51] Int. Cl.⁶ .................................................... A61C 3/00
[52] U.S. Cl. .................................................................. 433/8
[58] Field of Search .................... 433/8, 9, 17, 20

[56] References Cited

U.S. PATENT DOCUMENTS

| | | | |
|---|---|---|---|
| 3,930,311 | 1/1976 | Andrews | 433/8 |
| 5,232,361 | 8/1993 | Sachdeva et al. | 433/8 |
| 5,252,066 | 10/1993 | Fairhurst | 433/8 |
| 5,254,002 | 10/1993 | Reher et al. | 433/8 |
| 5,256,062 | 10/1993 | Griott | 433/9 |
| 5,358,402 | 10/1994 | Reed et al. | 433/8 |
| 5,595,484 | 1/1997 | Orikasa et al. | 433/8 |
| 5,597,302 | 1/1997 | Pospisil et al. | 433/8 |

*Primary Examiner*—John J. Wilson
*Attorney, Agent, or Firm*—Wood, Herron & Evans, L.L.P.

[57] ABSTRACT

An insert for reinforcing a nonmetallic orthodontic appliance is provided including a metal core member having a ceramic outer surface. In one preferred form, a ceramic coated metallic insert having a tooth enamel color is disposed within the archwire slot of a plastic bracket to form an aesthetically pleasing, reinforced plastic orthodontic bracket.

66 Claims, 2 Drawing Sheets

INSERT FOR REINFORCING AN ORTHODONTIC APPLIANCE AND METHOD OF MAKING SAME

FIELD OF THE INVENTION

This invention relates to orthodontic appliances, and more particularly, to reinforcing inserts for orthodontic appliances and appliances incorporating such inserts.

BACKGROUND OF THE INVENTION

In the field of orthodontics, patients increasingly have demanded orthodontic appliances which are less noticeable and more visually appealing than traditional metal appliances. Manufacturers of such appliances have responded to this demand by making orthodontic appliances out of alternative materials such as plastic and ceramic. While these alternative materials may be visually pleasing, they have some drawbacks. For example, plastic orthodontic appliances such as brackets and the like have been found to be unsatisfactory in some circumstances due to their inability to provide sufficient strength over long orthodontic treatment periods. Ceramics, on the other hand, are quite hard; however, they are brittle and thus subject to fracture under the stresses exerted during orthodontic treatment.

In order to improve the strength of such orthodontic appliances, it has been suggested to provide a reinforcing insert. For example, U.S. Pat. No. 5,254,002, commonly owned by the assignee of this application, discloses an orthodontic bracket having a main body portion made of a rigid, fiber reinforced plastic and including a rigid reinforcement molded into the body for strengthening the archwire slot. This reinforcing insert is made of either a metal, such as stainless steel, or a high strength ceramic material.

U.S. Pat. No. 5,358,402 discloses a ceramic orthodontic bracket having a metal archwire slot liner received in the archwire channel or slot. Although the ceramic body portion of this type of bracket may have a natural toothlike appearance, but the metal slot liner can detract from the overall aesthetic appearance of the bracket.

It would be desirable to have an improved insert for reinforcing orthodontic appliances that offers both improved aesthetic appeal and strength. Furthermore, it would be advantageous for such an insert to have enhanced biocompatibility and reduced frictional resistance to archwires and the like. It also would be beneficial to have an orthodontic appliance incorporating such an improved insert.

SUMMARY OF THE INVENTION

The subject matter of this application is related to that of copending patent application Ser. No. 08/722,741, entitled "METHOD OF ATTACHING A METALLIC INSERT TO A CERAMIC ORTHODONTIC OR DENTAL APPLIANCE", filed simultaneously herewith. The specification of that co-pending application is incorporated herein by reference in its entirety.

This invention offers the advantages of an extremely durable orthodontic insert which also is aesthetically pleasing. There is no need to compromise by choosing a reinforcing insert which offers high strength and low patient appeal or relatively lower strength and high patient appeal. Another benefit of the invention is improved biocompatibility. It is believed that some metals present biocompatibility problems when used in the mouth. However, the ceramic surface of the metal inserts of the present invention is biocompatible, thereby alleviating biocompatibility concerns. Furthermore, the insert has a reduced dynamic coefficient of friction, thereby enabling archwires and the like to move more easily across the insert's surface. This reduced coefficient of friction is made possible because the ceramic is deposited or formed on the insert in such a way as to create an extremely smooth ceramic surface.

In its broadest aspects, the invention is directed to an insert for reinforcing a nonmetallic orthodontic appliance, where the insert includes a metal core member having at least a partial ceramic outer surface. The metal core may be a stainless steel or a titanium alloy, and the ceramic may be an aluminum oxide, titanium nitride or titanium oxide. Preferably, the ceramic outer surface has a thickness of about 5,000 Å to about 50$\mu$, and a natural tooth enamel-like color. Furthermore, the ceramic typically has a dynamic coefficient of friction which is lower than that of the metal core member. The ceramic outer surface may be continuous over the entire metal core member or may be discontinuous, covering only portions of the metal core.

In another aspect, the invention is directed to an orthodontic appliance including a body portion and an insert as described above. The body portion may be made of a material such as plastic or ceramic, and if the appliance is a bracket, the bracket may include an archwire slot. The insert itself is associated with the body portion and reinforces the body portion of the orthodontic appliance. In the case of an orthodontic bracket, the insert may line the archwire slot or may be completely embedded within the body portion. If the insert lines the archwire slot, it may be at least partially exposed. Also, if the body portion includes one or more tiewings, the insert may include one or more corresponding flange sections associated with at least a portion of the tiewings for additional reinforcement. Furthermore, the flange sections may be either at least partially exposed or completely embedded within the tiewings.

In yet another aspect, the invention is directed to a method of making an insert for an orthodontic appliance, including forming a ceramic surface on a metal insert. In one such method, the metal insert may be made of a stainless steel or a titanium alloy, and the forming step includes depositing the ceramic onto the metal insert. The ceramic, typically an aluminum oxide, titanium nitride or titanium oxide, is deposited using a method such as plasma deposition, sputtering, ion beam implantation, chemical vapor deposition or physical vapor deposition. An alternate method of forming the ceramic surface includes reacting a titanium alloy metal insert with a gas such as oxygen or nitrogen to form the ceramic surface. Another method includes depositing a metallic material such as titanium, cobalt, zirconium, molybdenum, niobium, tantalum or alloys thereof onto a metal insert and subsequently reacting the deposited metallic material with a gas such as oxygen or nitrogen to form the ceramic surface. Yet another method of forming the ceramic surface includes anodizing a material onto the metal insert. Any reactive metallic material having a stable metallic oxide may be used, such as titanium, aluminum, zirconium, chromium and alloys thereof, for example.

In a further aspect, the invention relates to a method of making an improved orthodontic appliance, including forming the ceramic coated metal insert as described above and joining the coated insert with a nonmetallic orthodontic appliance.

These and other benefits and advantages of the invention will become readily apparent to those skilled in the art upon reviewing the following drawings and detailed description of the invention.

DETAILED DESCRIPTION OF THE INVENTION

Figure 1:
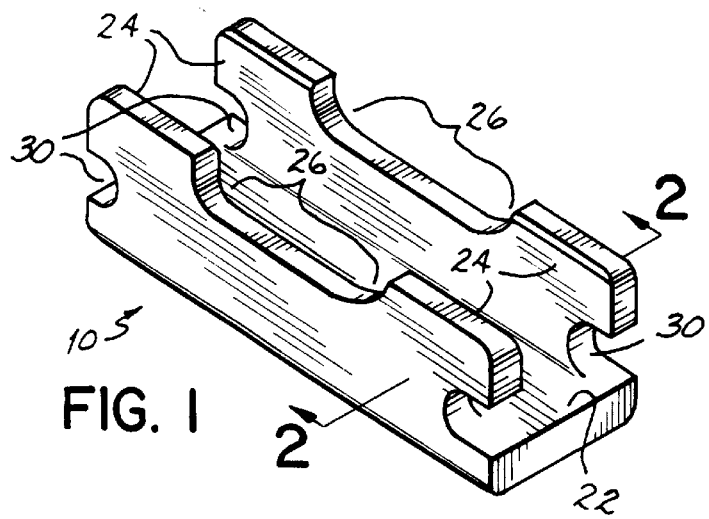
FIG. 1 is a perspective view of a ceramic coated metallic insert for reinforcing a nonmetallic orthodontic appliance.
Figure 2:
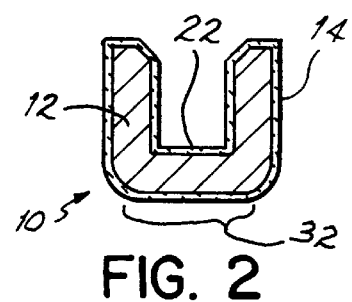
FIG. 2 is a cross-sectional view of the insert of FIG. 1 taken along line 2—2.

Referring to FIGS. 1 and 2, an insert 10 for reinforcing a nonmetallic orthodontic appliance includes a metal core member 12 having a ceramic outer surface 14. As used herein, the term "orthodontic appliance" refers to any device which may be adhered directly or indirectly to a tooth surface for the purpose of moving, aligning or fixing the position of a tooth or teeth. Nonlimiting examples include brackets, buccal tubes, and the like. The insert itself may be of any suitable size and shape, and may be spatially located on or in the nonmetallic orthodontic appliance in any position which assists in reinforcing the appliance. The material for the metal core member 12 may be any metallic based material which has the capability of being colored by a ceramic coating process and typically is a stainless steel, or a titanium-based or aluminum-based alloy. These materials are generally preferred because of their relative biocompatibility. The ceramic outer surface 14 preferably is a metallic oxide or nitride, such as an aluminum oxide, titanium oxide or titanium nitride, for example. However, any ceramic may be used to form the ceramic outer surface. For example, the ceramic may be carbon in crystalline form (e.g., diamond) or aluminum-titanium oxynitride.

Figure 5:
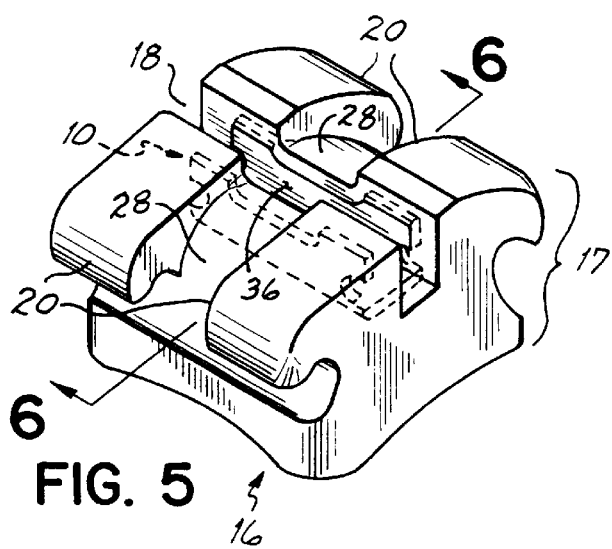
FIG. 5 is a perspective view of an improved orthodontic bracket incorporating the ceramic coated metallic insert of FIGS. 1 and 2.

The particular insert 10 shown is adapted to reinforce an orthodontic appliance such as a bracket 16 having a body portion 17 including an archwire slot 18, a pair of tiewings 20 and a connecting portion 28 linking the tiewings 20 as shown in FIG. 5. Therefore, the insert 10 includes a bottom wall 22 and two upstanding side walls 24 depending from the bottom wall 22. The side walls 24 of this insert 10 have mid-wall portions 26 which are slightly shorter than the remainder of the side walls 24 and which correspond to the connecting portions 28 of the bracket 16 of FIG. 5 which are somewhat shorter in height than the adjacent tiewings 20. Furthermore, the insert 10 shown includes a notched-out section 30 at the base of each of the terminal ends of the side walls 24. These notched-out sections 30 are particularly advantageous for an insert 10 which is formed in situ in an orthodontic appliance because the body portion of the appliance may flow into the space created by the notch, thereby creating a mechanical bond when the body portion hardens or cures.

Referring to FIG. 2, a preferred coated metallic insert 10 has a continuous ceramic outer surface 14 which is uniformly distributed over all exposed surfaces of the metal core member 12. The ceramic typically is a metallic oxide or nitride, and should have a color such as white which can blend in with the color of the teeth in order to provide improved aesthetics. In addition, the ceramic outer surface 14 preferably has a thickness of from about 5,000 Å to about 50μ.

While a continuous ceramic surface is preferred, it is not required. For example, an insert 10 may be formed without a ceramic surface 14 on the lower surface 32 of the insert bottom wall 22. Because the lower surface 32 typically is oriented toward a tooth when the orthodontic appliance is mounted in the mouth, this uncoated surface generally is not visible and should not detract from the aesthetics of the appliance. Nonetheless, it is preferable to provide a ceramic outer surface over all exterior surfaces of the metal core member because this ceramic coating also enhances the overall biocompatibility of the reinforcing insert.

Another advantage of the ceramic coated metallic insert is that the ceramic surface has a dynamic coefficient of friction which is lower than that of the bare metal core member. Therefore, when the coated insert is formed as an archwire slot liner disposed within the archwire slot of an orthodontic bracket, an archwire may transfer forces to the orthodontic bracket and across the orthodontic bracket to other brackets more easily.

Figure 3:
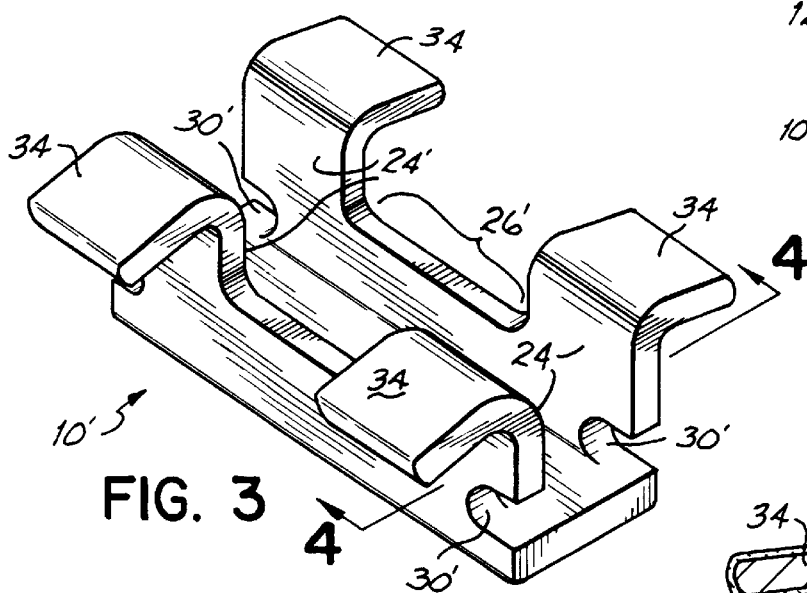
FIG. 3 is a perspective view of another embodiment of a ceramic coated metallic insert for reinforcing an orthodontic appliance.
Figure 4:
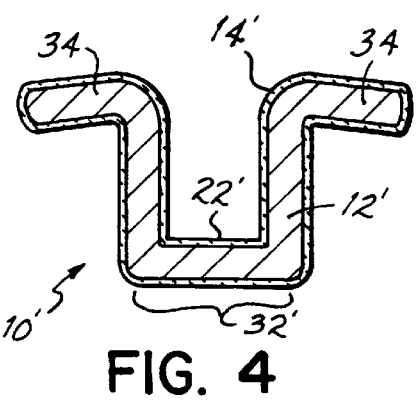
FIG. 4 is a cross-sectional view of the insert of FIG. 3 taken along line 4—4.
Figure 7:
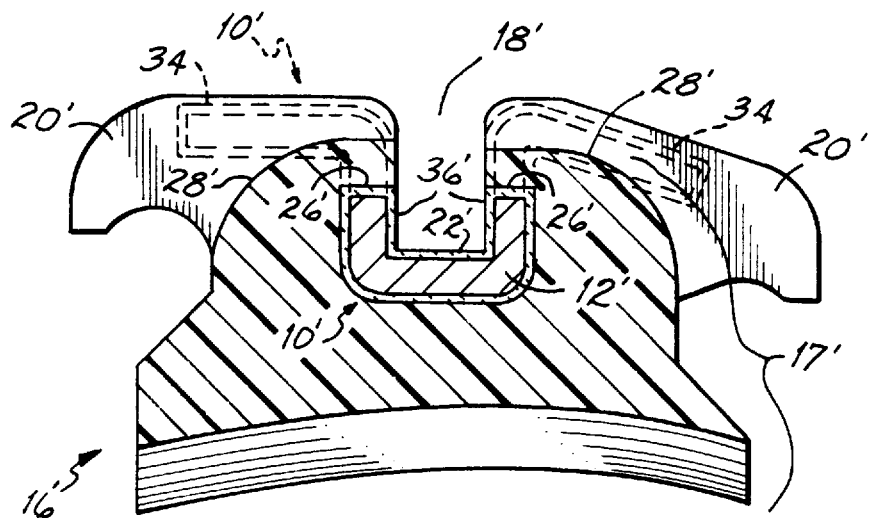
FIG. 7 is a cross-sectional view similar to FIG. 6 but of an improved orthodontic bracket incorporating the ceramic coated metallic insert substantially as shown in FIGS. 3 and 4.

Referring to FIGS. 3 and 4, another preferred embodiment of the ceramic coated metallic insert 10' further includes two sets of oppositely oriented flanges 34 which are adapted to extend at least partially into each tiewing 20' of an orthodontic bracket 16' as shown in FIG. 7, thereby strengthening the tiewings 20' and making them more resistant to occlusion forces such as chewing which may otherwise deform the wings 20' over time. In the particular embodiment shown in FIGS. 3 and 4, the metal core member 10'0 has a ceramic outer surface 14' which covers all portions of the metal core member 12', including the lower surface 32' of the bottom wall 22'.

The metal core member of the coated insert may be made by conventional metal forming techniques, such as standard sheet metal forming and cutting techniques. For example, an insert or inserts may be cut from a sheet of metal so as to form a plurality of blanks which provide the laid out configuration of the bottom wall and side walls of the insert. This method of forming a bare metallic insert is taught in U.S. Pat. No. 5,254,002 (the '002 patent) which is incorporated herein in its entirety by reference. As disclosed in the '002 patent, the insert may be attached to a main handling section of the blank by a narrow gate, which may form a part of the bottom wall of the insert itself. The two side walls of the insert are then folded upward using standard sheet metal forming methods to form a generally a U-shaped insert.

The ceramic outer surface of the coated metallic insert may be formed on the now U-shaped metal core member in a number of different ways. For example, in one method the ceramic surface is formed by depositing a ceramic material onto the metallic insert. With this particular method, the metal insert preferably is made of a stainless steel or a titanium-based alloy. The ceramic deposited onto the insert may be any ceramic compound which is a combination of a gas and a metal. Typically, this ceramic is a metallic oxide or nitride such as an aluminum oxide, a titanium oxide, a titanium nitride or the like. This ceramic material may be deposited onto the metallic insert using any one of a number of different deposition methods, including, for example, plasma deposition, sputtering, ion beam implantation, chemical vapor deposition or physical vapor deposition.

Another method for forming the ceramic surface on the metallic insert includes reacting a metallic insert made of a titanium-based alloy with a gas to form the ceramic surface. Preferably, the gas is oxygen or nitrogen, in which case the ceramic surface formed will be a metallic oxide or nitride, such as an aluminum oxide, titanium oxide or titanium nitride.

Yet another method for forming the ceramic surface on the metallic insert includes depositing a metallic material onto the bare metal insert and thereafter reacting the deposited metal material with a gas to form the ceramic surface. The deposited metallic material preferably is titanium, cobalt, zirconium, molybdenum, niobium, tantalum or an alloy thereof, which may be deposited using any of a number of deposition methods such as plasma deposition, sputtering, ion beam implantation, chemical vapor deposition or physical vapor deposition. Furthermore, the gas used to react with the deposited metal material typically is oxygen or nitrogen, in which case the ceramic coating formed is a metallic oxide or nitride as described above. Yet another method of forming the ceramic surface includes anodizing a material onto the metal insert. Any reactive metallic material having a stable metallic oxide may be used, such as titanium, aluminum, zirconium, chromium and alloys thereof, for example.

Once the ceramic surface has been formed on the metal core member, the coated metallic insert may be joined with a nonmetallic orthodontic appliance to form an improved and reinforced orthodontic appliance. If the orthodontic appliance is to be made of plastic, the coated metallic insert may be placed in an injection mold cavity and the plastic material may be molded around the insert to form a body portion, as is taught in the '002 patent. Preferably, the plastic is polycarbonate with reinforcing glass fibers as taught in the '002 patent, with 20% to 40% by weight of glass fibers being preferred. The orthodontic appliance then may be removed from the mold and any excess sheet metal such as a main handling section, may be trimmed from the improved, reinforced appliance. However, if the orthodontic appliance is to be formed of ceramic, then the ceramic coated metallic insert is joined in a different fashion. Preferably, the coated metallic insert is joined with the appliance using an adhesive, as taught in co-pending patent application Ser. No. 08/722,741, entitled "METHOD OF ATTACHING A METALLIC INSERT TO A CERAMIC ORTHODONTIC OR DENTAL APPLIANCE" filed on even date herewith, which is hereby incorporated herein in its entirety by reference.

Figure 6:
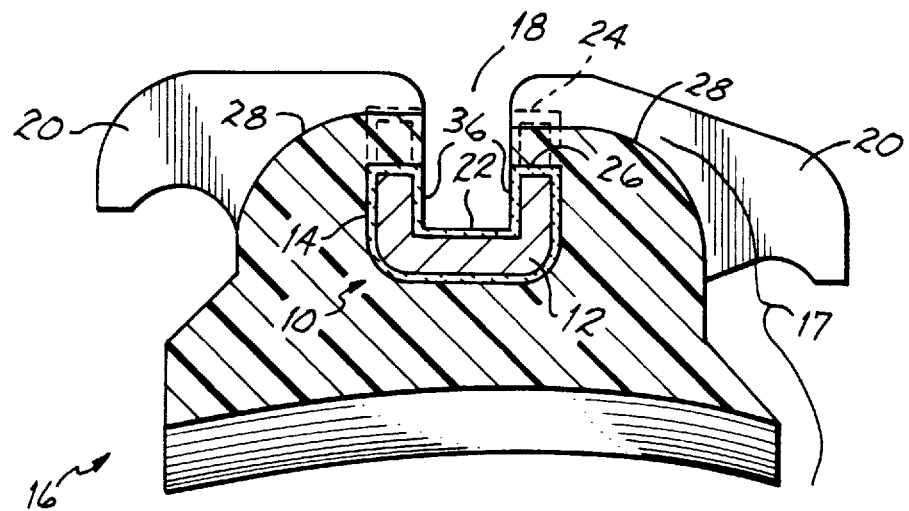
FIG. 6 is a cross-sectional view of the improved orthodontic bracket of FIG. 5 taken along line 6—6.

Referring to FIGS. 5–6, an improved orthodontic bracket 16 is shown having a ceramic coated metallic insert 10. In this particular embodiment, the bracket 16 includes a body portion 17 having a pair of tiewings 20, a connecting portion 28 linking the tiewings 20 and an archwire slot 18. As best shown in FIG. 6, the coated metallic insert 10 is slightly recessed into the body portion 17 of the bracket 16 so that the inner side wall surfaces 36 of the insert 10 are substantially flush with the archwire slot 18. Referring to FIG. 7, yet another preferred embodiment of the improved orthodontic bracket 16' includes a coated metal insert 10' having flanges 34 which extend at least partially into each tiewing 20'. Preferably, these flanges 34 are completely embedded within the tiewings as shown, however, this is not required.

It is to be understood that various changes and modifications may be made from the embodiments discussed above without departing from the scope of the present invention, which is defined by the following claims.

What is claimed is:

1. An orthodontic appliance, comprising:
   a non-metallic body portion; and
   a reinforcing insert attached to said body portion for reinforcing said body portion, said insert including a metal core member having a ceramic outer surface.

2. The appliance of claim 1 wherein said body portion comprises a material selected from the group consisting of plastic and ceramic.

3. The appliance of claim 1 wherein said body portion comprises ceramic, said metal core member ceramic outer surface existing independently of said body portion ceramic.

4. The appliance of claim 3 wherein said metal core member includes a metal selected from the group consisting of stainless steels and titanium based alloys.

5. The appliance of claim 4 wherein said ceramic outer surface includes a ceramic selected from the group consisting of aluminum oxides, titanium nitrides and titanium oxides.

6. The appliance of claim 5 wherein said ceramic outer surface has a thickness in the range of from about 5,000 Å to about 50μ.

7. The appliance of claim 6 wherein said ceramic outer surface has a natural tooth-enamel-like color.

8. The appliance of claim 7 wherein said ceramic outer surface has a dynamic coefficient of friction lower than that of said metal core member.

9. The appliance of claim 1 wherein said metal core member includes a metal selected from the group consisting of stainless steels and titanium based alloys.

10. The appliance of claim 1 wherein said ceramic outer surface includes selected from the group consisting of aluminum oxides, titanium nitrides and titanium oxides.

11. The appliance of claim 1 wherein said ceramic outer surface has a thickness in the range of from about 5,000 Å to about 50μ.

12. The appliance of claim 1 wherein said ceramic outer surface has a natural tooth-enamel-like color.

13. The appliance of claim 1 wherein said ceramic outer surface has a dynamic coefficient of friction lower than that of said metal core member.

14. The appliance of claim 1 wherein said body portion includes an archwire slot.

15. The appliance of claim 14 wherein said insert lines said archwire slot and is at least partially exposed.

16. The appliance of claim 15 wherein said insert includes a plurality of inner side wall surfaces, said inner side wall surfaces being substantially flush with said archwire slot.

17. The appliance of claim 14 wherein said insert is completely embedded within said body portion.

18. The appliance of claim 14 wherein said body portion further includes a tiewing, and said insert including a flange section attached to at least a portion of said tiewing for reinforcing said tiewing.

19. The appliance of claim 18 wherein said flange section is completely embedded within said tiewing.

20. The appliance of claim 18 wherein said flange section is at least partially exposed.

21. The appliance of claim 14 wherein said insert is attached to said archwire slot.

22. The appliance of claim 1 wherein said ceramic outer surface is continuous.

23. The appliance of claim 1 wherein said ceramic outer surface is discontinuous.

24. The appliance of claim 23 wherein said insert includes a bottom wall having a lower surface, said lower surface being substantially free of said ceramic outer surface.

25. The appliance of claim 1 wherein said insert includes a bottom wall and two upstanding side walls depending from said bottom wall.

26. The appliance of claim 25 wherein at least one of said side walls includes a mid-wall portion which is shorter than the remainder of said one of said side walls.

27. The appliance of claim 25 wherein at least one of said sidewalls includes a base having a terminal end, said base further including a notched-out section.

28. The appliance of claim 25 wherein said insert includes at least one flange depending from one of said two upstanding side walls.

29. The appliance of claim 25 wherein said ceramic outer surface covers at least a portion of said bottom wall.

30. The appliance of claim 25 wherein said ceramic outer surface covers at least a portion of one of said two upstanding side walls.

31. The appliance of claim 25 wherein said ceramic outer surface covers at least a portion of each of said two upstanding side walls.

32. A method of making an orthodontic appliance, comprising the steps of:
forming a ceramic outer surface on a metal core member comprising a metal, thereby forming a reinforcing insert; and
joining said insert with a non-metallic orthodontic appliance body portion.

33. The method of claim 32 wherein said metal is selected from the group consisting of stainless steels and titanium based alloys.

34. The method of claim 33 wherein said forming step includes depositing a ceramic onto said metal core member.

35. The method of claim 34 wherein said ceramic is selected from the group consisting of aluminum oxides, titanium nitrides and titanium oxides.

36. The method of claim 34 wherein said ceramic is deposited using a method selected from the group consisting of plasma deposition, sputtering, ion beam implantation, chemical vapor deposition and physical vapor deposition.

37. The method of claim 32 wherein said metal core member includes a titanium alloy and said forming step includes reacting said metal with a gas to form said ceramic surface.

38. The method of claim 37 wherein said gas is selected from the group consisting of oxygen and nitrogen.

39. The method of claim 38 wherein said formed ceramic outer surface is selected from the group consisting of aluminum oxides, titanium nitrides and titanium oxides.

40. The method of claim 32 wherein said forming step includes depositing a metallic material selected from the group consisting of titanium, cobalt, zirconium, molybdenum, niobium, tantalum and alloys thereof onto said metal core member and thereafter reacting said deposited metallic material with a gas to form said ceramic outer surface.

41. The method of claim 40 wherein said gas is selected from the group consisting of oxygen and nitrogen.

42. The method of claim 41 wherein said formed ceramic outer surface is selected from the group consisting of aluminum oxides, titanium nitrides and titanium oxides.

43. The method of claim 32 wherein said forming step includes anodizing a material onto said metal core member to form said ceramic surface.

44. The method of claim 43 wherein said material is selected from the group consisting of titanium, aluminum, zirconium, chromium and alloys thereof.

45. The method of claim 32 wherein said body portion comprises plastic.

46. The method of claim 32 wherein said body portion comprises ceramic, said metal core member ceramic outer surface existing independently of said body portion ceramic.

47. The method of claim 32 wherein said body portion includes an archwire slot.

48. The method of claim 47 wherein said insert lines said archwire slot and is at least partially exposed.

49. The method of claim 48 wherein said insert includes a plurality of inner side wall surfaces, said inner side wall surfaces being substantially flush with said archwire slot.

50. The method of claim 47 wherein said insert is completely embedded within said body portion.

51. The method of claim 47 wherein said body portion further includes a tiewing, and said insert including a flange section attached to at least a portion of said tiewing for reinforcing said tiewing.

52. The method of claim 51 wherein said flange section is completely embedded within said tiewing.

53. The method of claim 51 wherein said flange section is at least partially exposed.

54. The method of claim 47 wherein said insert is attached to said archwire slot.

55. The method of claim 32 wherein said ceramic outer surface has a thickness in the range of from about 5,000 Å to about 50μ.

56. The method of claim 32 wherein said ceramic outer surface has a dynamic coefficient of friction lower than that of said metal core member.

57. The method of claim 32 wherein said ceramic outer surface is continuous.

58. The method of claim 32 wherein said ceramic outer surface is discontinuous.

59. The method of claim 58 wherein said insert includes a bottom wall having a lower surface, said lower surface being substantially free of said ceramic outer surface.

60. The method of claim 32 wherein said insert includes a bottom wall and two upstanding side walls depending from said bottom wall.

61. The method of claim 60 wherein at least one of said side walls includes a mid-wall portion which is shorter than the remainder of said one of said side walls.

62. The method of claim 60 wherein at least one of said sidewalls includes a base having a terminal end, said base further including a notched-out section.

63. The method of claim 60 wherein said insert includes at least one flange depending from one of said two upstanding side walls.

64. The method of claim 60 wherein said ceramic outer surface covers at least a portion of said bottom wall.

65. The method of claim 60 wherein said ceramic outer surface covers at least a portion of one of said two upstanding side walls.

66. The method of claim 60 wherein said ceramic outer surface covers at least a portion of each of said two upstanding side walls.

* * * * *